United States Patent [19]

Izuhara et al.

[11] Patent Number: 4,868,180

[45] Date of Patent: Sep. 19, 1989

[54] VITAMIN-CONTAINING GRANULES AND PRODUCTION THEREOF

[75] Inventors: Seiji Izuhara, Tondabayashi; Nobuyuki Kitamori; Masaya Maeno, both of Suita, all of Japan

[73] Assignee: Takeda Chemical Industries, Ltd., Osaka, Japan

[21] Appl. No.: 915,125

[22] Filed: Oct. 1, 1986

[30] Foreign Application Priority Data

Oct. 7, 1985 [JP] Japan .................................. 224079

[51] Int. Cl.$^4$ .................. A61K 31/525; A61K 31/44; A61K 31/195; A61K 47/00
[52] U.S. Cl. ...................................... 514/251; 514/345; 514/355; 514/563; 514/781
[58] Field of Search ............... 514/251, 345, 355, 563, 514/781

[56] References Cited

U.S. PATENT DOCUMENTS

| | | | |
|---|---|---|---|
| 3,308,217 | 3/1967 | Lowy | 514/251 |
| 3,493,659 | 2/1970 | Magid | 424/280 |
| 3,907,983 | 9/1975 | Seth | 424/35 |
| 4,036,948 | 7/1977 | Kitamori et al. | 424/32 |
| 4,372,968 | 2/1983 | Kitamori et al. | 424/280 |
| 4,486,435 | 12/1984 | Schmidt et al. | 514/276 |
| 4,619,829 | 10/1986 | Motschan | 514/251 |
| 4,702,918 | 10/1987 | Ushimaru et al. | 514/724 |
| 4,702,919 | 10/1987 | Kitamori et al. | 514/276 |

FOREIGN PATENT DOCUMENTS 678143  1/1964  Canada ................................ 514/251

*Primary Examiner*—Douglas W. Robinson
*Assistant Examiner*—Raymond J. Henley, III
*Attorney, Agent, or Firm*—Wenderoth, Lind & Ponack

[57] ABSTRACT

A vitamin-containing granule comprising one or more compounds selected from the group consisting of vitamin $B_6$, vitamin $B_2$, nicotinamide and a pantothenic acid salt, and a binding agent, said compound or compounds accounting for 90 to 99 weight percent of the granules on the dry basis, can be prepared by spray-coating the powders of said compound or compounds with a solution containing a binder while maintaining the powders in a fluidized state in a fluidized-bed granulation apparatus.

The granules are highly flowable and blend well with other medicaments, granules, additives, and so on. In addition to this, the granules are excellent in compressibility so that they can be processed into tablets with small amounts of excipients, and the tablets therefrom have satisfactory high hardness.

8 Claims, No Drawings

VITAMIN-CONTAINING GRANULES AND PRODUCTION THEREOF

The present invention relates to a granule for direct compression containing one or more compounds selected from the group consisting of vitamin $B_6$, vitamin $B_2$, nicotinamide and a pantothenic acid salt, a process for preparation thereof, and tablets produced therefrom.

Vitamin $B_6$, vitamin $B_2$, nicotinamide and calcium pantothenate are often administered alone or in combination with other vitamins and/or drugs in the form of tablets. Tablets are generally prepared by compression of powders as such or after preliminary granulation.

It would be expedient if tablets could be produced directly from powders without preliminary granulation. However, vitamin $B_6$, vitamin $B_2$, nicotinamide and calcium pantothenate are lacking in flowability and compressibility which are necessary for tableting and, therefore, cannot be compressed directly from powders. For this reason, vitamin $B_6$, vitamin $B_2$, nicotinamide, and calcium pantothenate are granulated in combination with other vitamins, pharmacollogically active substances and/or excipients by a conventional wet kneading granulation process and, then, compressed into tablets from the resulting granules.

The wet granulation of vitamin $B_6$, vitamin $B_2$, nicotinamide and calcium pantothenate can hardly give a homogenous granule. The granules so produced are not very good in flowability. Tablets obtained therefrom are not satisfactory in mechanical strength. Furthermore, granules obtained by the wet granulation demand a large amount of excipient in the tableting step and this leads to a great increase in the tablet weight, resulting in difficulty in taking the tablet.

The present inventors conducted an intensive research to overcome the above-mentioned disadvantages and found that the granulation of powders of vitamin $B_6$, vitamin $B_2$, nicotinamide, and calcium pantothenate in a fluidized bed granulator using a small amount of a binding agent can produce granules capable of being tableted with a small quantity of an excipient and the granules give tablets having a satisfactory high hardness. The findings were followed by a further investigation which has resulted in the present invention.

Thus, the present invention is concerned with (1) a vitamin-containing granule comprising one or more compounds selected from the group consisting of vitamin $B_6$, vitamin $B_2$, nicotinamide and a pantothenic acid salt and a binding agent, with said compound or compounds accounting for about 90 to 99 weight percent of the granules on the dry basis, (2) a process for preparation of vitamin-containing granules which comprises fluidizing powders of one or more compounds selected from the group consisting of vitamin $B_6$, vitamin $B_2$, nicotinamide and a pantothenic acid salt, at least about 95 weight percent of said powders passing a 100-mesh sieve (JIS), in a fluidized bed granulator and spraying the powders so fluidized with a solution containing about 1 to 10 weight percent of a binding agent based on the total dry weight of product granules, and (3) a tablet produced by compressing a tablet mixture containing granules comprising one or more compounds selected from the group consisting of vitamin $B_6$, vitamin $B_2$, nicotinamide and a pantothenic acid salt and a binding agent, said compound or compounds accounting for about 90 to 99 weight percent of the granules on the dry basis.

As examples of said vitamin $B_6$, there may be mentioned pyridoxine hydrochloride, pyridoxal phosphate and the like. As examples of said vitamin $B_2$, there may be mentioned riboflavin and the like. The salt of pantothenic acid usable in the present invention is exemplified by calcium pantothenate and the like.

The vitamin $B_6$, vitamin $B_2$, nicotinamide, and pantothenic acid salt are used in powdery form. Thus, powders such that about 95 weight % or more of the particles pass a 100-mesh sieve (JIS) are used. More desirable are powders such that all the particles pass the 100-mesh sieve (JIS) and at least about 50 weight percent of the particles pass a 280-mesh sieve (JIS).

The fluidized-bed granulator is a fluidized-bed dryer fitted with a binder solution spraying means and permits simultaneous granulation and drying operations in a single unit. As examples of such an apparatus, there may be mentioned models available on the market under the names Glatt (Glatt AG in West Germany; Fuzi Powdal Co. in Japan), Aeromatic (Aeromatic AG in Switzerland), Calmic (Calmic Engineering Co. in England), Flow Coater (Freund Industries Co. in Japan) and other machines.

The binding agent for spray coating is a water-soluble binder or a binder soluble in an organic solvent. The water-soluble binder is exemplified by pregelatinized starch, water-soluble celluloses, water-soluble high polymer and so on. The pregelatinized starch means a starch prepared by heating a dispersion of starch in water or a dry starch obtained by drying the same. The pregelatinized starch is exemplified by pregelatinized corn starch, pregelatinized potato starch, pregelatinized modified starch [e.g. those described in Code of Federal Regulations (U.S.A) 121, 1031 a, b, c, d, e, f, g and h.]. It may also be a pregelatinized dry commercial product such as Amycol C (Nichiden Chemical Co. in Japan), Amylox (Nihon Corn Starch Co. in Japan), Pre-Gel (Hublinger Co. in U.S.A.), or Instant Cleargel (National Starch Co. in U.S.A.).

The water-soluble celluloses include, for example, hydroxypropylcellulose, hydroxymethylcellulose, hydroxypropylmethylcellulose, carboxymethylcellulose, methylcellulose and the like. The water soluble high molecular weight compounds are exemplified by polyvinylpyrrolidone (M.W. 10,000–100,000), polyvinyl alcohol(M.W. 10,000–50,000), dextrin, gum arabic, gelatin, polydextrose and the like.

The binding agent soluble in organic solvents may for example be a cellulose derivative soluble in organic solvents, such as cellulose acetate phthalate, hydroxypropylmethylcellulose phthalate, ethylcellulose and so on. Among them, the water-soluble binder, especially water-soluble celluloses are preferably used.

The solvent used in preparing a solution containing a binding agent for spraying includes, among others, water and organic solvents, for example, lower alcohols (e.g. methyl alcohol, ethyl alcohol, isopropyl alcohol, etc.). ketones (e.g. acetone, etc.).

The binding agent may be used in a useful and manageable concentration, for example about 1 to 15 weight percent of the binder solution and preferably 3 to 10 weight percent of the binder solution. The optimum concentration depends on the combination of binding agent and solvent and is desirably such that it gives a sprayable viscosity which may range from about 1 to 1000 centipoise, preferably about 10 to 500 centipoise.

The granulation is carried out by spray-coating vitamin powder with a solution containing a binder, while allowing the powder to fluidize in a fluidized-bed granulator until the amount of the binder has reached about 1 to 10 weight percent relative to the vitamin component. The vitamin powders are charged into a fluidized-bed apparatus and fluidized by feeding a dry air heated up to about 50° to 100° C. through the lower part of the apparatus. Then, a solution containing a binder is sprayed from spray nozzles towards the powders in fluidized state. The exhausted air temperature is normally maintained at about 30° to 60° C. The conditions for spray-coating and granulation can be controlled by adjusting the air feeding rate, air temperature, solution spray rate, operating time and so on. Granulation is generally complete in 10 minutes to 2 hours.

After granulation, drying is carried out in a conventional manner. Thus, they can be dried by continuing the fluidization after completion of spraying until the product temperature reaches a predetermined level, for example, 30° to 60° C.

The dried product can be used as final granules but can be adjusted to a desired granule size distribution by milling the granules in a Power mill, Fitz mill or the like.

In this manner, vitamin granules containing about 90 to 99 weight percent of vitamin $B_6$, vitamin $B_2$, nicotinamide and/or pantothenic acid salt on the dry basis can be obtained.

Among the vitamin-containing granules according to the present invention, particularly preferred are granules containing about 95 to 98 weight percent of at least one compound selected from the group consisting of vitamin $B_6$, vitamin $B_2$, nicotinamide and pantothenic acid salt on the dry basis. While there is no particular limitation on granule size, excessively coarse particles would not be suitable for blending with other particulate components and could cause weight fluctuation in tablet manufacturing. Excessively fine particles would also prove disadvantageous because of their poor flowability in charging into dies in tableting. The desired granule size is such that the proportion of particles which do not pass a 32-mesh sieve (JIS) is not more than 5 weight percent and that of particles which pass a 145-mesh sieve (JIS) is not more than 30 weight percent.

The vitamin granules according to the present invention are used as a raw material for the manufacture of tablets containing one or more members of vitamin $B_6$, vitamin $B_2$, nicotinamide and pantothenic acid salt.

The tableting of the granules is carried out in accordance with the conventional pharmaceutical procedure under the routine tableting conditions (e.g. 800 to 2500 kg/cm$^2$) in the presence of a lubricating agent and, as required, other drugs and/or excipients (e.g. lactose, sucrose, mannitol, etc.). The lubricating agent may be those commonly used in the manufacture of tablets, such as stearic acid compounds (e.g. magnesium stearate, calcium stearate, stearic acid, etc.), talcs, sucrose fatty acid esters, and so on. The amount and type of lubricating agent are selected so that the resulting tablet will be useful and marketable in respect of strength and disintegrability. Generally, its amount is preferably about 0.1 to about 7 weight percent based on the active component of the product tablet, and it is preferable that said stearic acid compound is added in a proportion of at least about 0.5 percent.

The drugs other than the above-mentioned active compounds that can be additionally incorporated include, among others, L-ascorbic acid, sodium L-ascorbate, vitamin $B_1$ hydrochloride, and so on. These drugs are preferably used in the form of granules, which have been prepared by coating the respective powders with the aid of a binding agent in a fluidized-bed granulator (see U.S. Pat. Nos. 4,036,948 and 4,372,968, and European Patent (Laid-Open) No. 0178138).

By the method according to the present invention, there can be obtained granules comprising vitamin B group particles uniformly coated with a small amount of a binding agent and tablets containing vitamin B group compounds in high concentrations can be obtained by a simple procedure comprising mixing said granules with a lubricating agent, etc. and tableting by compressing the mixture. The granules do not include fine dust and have good flowability. This quality is desirable for direct compression, makes for ease of handling, and allows for a minimum of swirling dust. In addition, the granules have good mixability with other ingredients or granules. The granules of the present invention, though having a very low binder content, have good stability even after mixing with other ingredients or granules, show good bonding property, and have good compressibility, because the surface of the vitamin powder is uniformly coated. Therefore, the granules require only a small amount of an excipient in the manufacture of tablets and this contributes to a reduction in tablet size. This feature is suitable for the manufacture of a multi-vitamin preparation and ensures stability in isolation from the other vitamins. Furthermore, thanks to their improved binding property, the use of these granules ensures the overall hardness of tablets.

Thus, whether the product is a tablet containing vitamin B alone or a tablet containing vitamin B and other medicaments, the required amount of excipient may be only very low (for example, 1 to 10 weight percent based on the total weight of the tablet).

Moreover, as these granules are lean in a binder component, the tablets manufactured from the granules can be small in size and yet have sufficient mechanical strength. The disintegration of the tablets is also rapid. Thus, these and other excellent qualities can be ensured. Furthermore, the granules according to the present invention are characterized in that the characteristic bitter taste of vitamin B compounds has been ameliorated. Therefore, the tablets manufactured in accordance with the present invention can be easily ingested.

The term "mesh" as used herein means the sieve size according to the classification defined in Japan Industrial Standard (JIS). The relation between mesh designation and sieve size is shown in the following table.

| Mesh | Size of sieve openings ($\mu$) |
| --- | --- |
| 32 | 500 |
| 100 | 149 |
| 120 | 125 |
| 145 | 105 |
| 200 | 77 |
| 280 | 53 |
| 325 | 44 |

EXAMPLES

The following examples are given to illustrate the present invention in further detail. In the following description, all parts are by weight.

EXAMPLE 1

While 97 parts of pyridoxine hydrochloride powders passing a 100-mesh sieve (JIS) were fluidized in a fluidized bed granulator using dry air at 80° to 100° C., a 5 weight % aqueous solution containing hydroxymethylcellulose was sprayed to the fluidized powders up to an amount equivalent to 3 parts on the solid basis, and the granules obtained were allowed to dry in the granulator. The resulting granulation was pulverized in a Fitz mill using a punched screen with openings 1.5 mm in diameter to give pyridoxine hydrochloride-containing granules. The particle size distribution of the resulting granules was such that 5.0% of them remained on a 32-mesh sieve (JIS) and another 0.5% of them passed a 120-mesh sieve (JIS). As shown in the following table, the bitter taste of the ungranulated material had been mitigated in the product granules.

Results of a sensory test of pyridoxine hydro-chloride-containing granules:

|  | (Evaluation by a panel of 10 tasters) | | | | | | | | | | Overall evaluation |
|---|---|---|---|---|---|---|---|---|---|---|---|
|  | Panelist | | | | | | | | | | |
|  | 1 | 2 | 3 | 4 | 5 | 6 | 7 | 8 | 9 | 10 | |
| Granules | ± | ± | ± | ± | ± | ± | ± | ± | ± | ± | ± |
| Ungranulated material | + | + | + | + | + | + | + | + | + | + | + |

Criteria:
±: Almost no bitter taste is felt.
+: A bitter taste is felt.

EXAMPLE 2

The procedure of Example 1 was repeated except that a 5 weight % aqueous solution containing hydroxypropylcellulose was used as the binder solution to produce pyridoxine hydrochloride-containing granules. The granule size distribution of the product was such that 5.4% remained on a 32-mesh sieve (JIS) and 6.5% passed a 120-mesh sieve (JIS).

EXAMPLE 3

While 97 parts of pyridoxal phosphate powders passing a 100-mesh sieve (JIS) were fluidized in a fluidized-bed granulator using dry air at 80° to 100° C., a 5 weight % aqueous solution containing hydroxypropylcellulose was sprayed to the fluidized powders up to an amount equivalent to 3 parts on the solid basis and the resultant granules were allowed to dry in the granulator. The resulting product was pulverized in a Fitz mill using a 1.5 mm screen to give pyridoxal phosphate-containing granules. These granules were such that 2.5% remained on a 32-mesh sieve (JIS) and 7.1% passed a 145-mesh sieve (JIS).

EXAMPLE 4

While 97 parts of nicotinamide powders passing a 120-mesh sieve were fluidized in a fluidized-bed granulator using dry air heated up to 80°-100° C., a starch paste which had been prepared by dispersing 6 weight % of corn starch in water and gelatinizing it at 75° C. was sprayed to the fluidized powders up to an amount equivalent to 3 parts on the solid basis and the granules were dried as such in the granulator. The resulting product was pulverized in a Fitz mill using a punched screen with openings 1.5 mm in diameter to give nicotinamide-containing granules. The particle size distribution was such that 4.5% of the product remains on a 32-mesh sieve (JIS) and 2.3% passes a 145-mesh sieve (JIS).

EXAMPLE 5

The procedure of Example 4 was repeated except that a 5 weight % aqueous solution containing hydroxypropylmethylcellulose was used as the binder solution to give nicotinamide-containing granules. The particle size disdistribution of the product was such that 3.0% remained on a 32-mesh sieve (JIS) and 7.4% passed a 145-mesh sieve (JIS).

EXAMPLE 6

While 97 parts of calcium pantothenate powders passing a 100-mesh sieve (JIS) were fluidized in a fluidized-bed granulator using dry air heated up to 80° to 90° C., a 5 weight % aqueous solution containing hydroxypropylcellulose was sprayed to the fluidized powder up to an amount equivalent to 3 parts on the solid basis and the granules were allowed to dry in the granulator. The resulting product was pulverized in a Fitz mill using a punched screen with openings 1.5 mm in diameter to give calcium pantothenate-containing granules. The particle size distribution of the product was such that 2.1% remained on a 32-mesh sieve (JIS) and 6.7% passed a 145-mesh sieve (JIS).

EXAMPLE 7

While 97 parts of riboflavin powders passing a 100-mesh sieve (JIS) were fluidized in a fluidized bed granulator using dry air heated up to 50 ° to 100° C., a 5 weight % aqueous solution containing hydroxypropylmethylcellulose was sprayed to the fluidized powders up to an amount equivalent to 3 parts on the dry basis, and the granules obtained were allowed to dry in the granulator. The resulting granules were pulverized in a Fitz mill using a punched screen with openings 1.5 mm in diameter to give riboflavin-containing granules. The granule size distribution of the resulting granules was such that 3.5% of them remained on a 32-mesh sieve (JIS) and another 2.3% of them passed a 145-mesh sieve (JIS).

EXAMPLE 8

While 95 parts of pyridoxine hydrochloride powders passing a 100-mesh sieve (JIS) were fluidized in a fluidized-bed granulator using dry air heated up to 70° to 100° C., a 10 weight % aqueous solution containing hydroxypropylmethylcellulose was sprayed to the fluidized powders up to an amount equivalent to 5 parts on the solid basis and the granules produced were allowed to dry in the granulator. The resulting product was pulverized in a Fitz will to give pyridoxine hydrochloride-containing granules. The particle size distribution of the product was such that 4.9% remained on a 32-mesh sieve (JIS) and 0.4% passed a 120 mesh-sieve (JIS).

REFERENCE EXAMPLE

While 97 parts of calcium ascorbate powders passing a 120-mesh sieve (JIS) were fluidized in a fluidized bed granulator using dry air heated up to 50° to 100° C., a 5 weight % aqueous solution containing hydroxylpropylmethylcellulose was sprayed to the fluidized powders up to an amount equivalent to 3 parts on the dry basis, and the granules were allowed to dry in the granulator. The resulting granules were pulverized in a Fitz mill using a punched screen with openings 1.5 mm in diameter to give calcium ascorbate-containing granules. The granule size distribution of the resulting granules was such that 0% of them remained on a 16-mesh sieve (JIS) and another 4.7% of them passed a 120-mesh sieve (JIS).

EXAMPLE 9

To 103.1 parts of the pyridoxine hydrochloride-containing granules as obtained in Example 1 were added 11.8 parts of corn starch and 0.1 part of magnesium stearate. The mixture was compressed into tablets having a diameter of 7.0 mm and weighing 115 mg per tablet. Each tablet contained 100 mg of pyridoxine hydrochloride and had a hardness of 6.2 kg as determined with a Heberlein hardness tester. The disintegration time was 4.5 minutes as measured by the method according to the Japanese Pharmacopeia.

EXAMPLE 10

31.0 parts of the pyridoxine hydrochloride-containing granules as obtained in Example 2 were mixed with 31.0 parts of thiamine nitrate-containing granules (as prepared based on Example 2 of European Patent (Laid-Open) No. 0178138), 7.5 parts of 0.1% vitamin $B_{12}$ (cyanocobalamin) trituration [Roche, U.S.A.], 7.88 parts of crystalline cellulose, and 0.12 parts of magnesium stearate. The mixture was compressed into tablets weighing 235 mg per tablet. Each tablet had a diameter of 8.5 mm and contained 100 mg of pyridoxine hydrochloride, 100 mg of thiamine nitrate, and 25 mcg of cyanocobalamin. As determined with a Heberlein hardness tester, the hardness of the tablets was 8.5 kg. The disintegration time determined by the method of the Japanese Pharmacopeia was 9.6 minutes.

EXAMPLE 11

30 parts of pyridoxal phosphate-containing granules as obtained in Example 3, 20 parts of spray-dried lactose, 18.8 parts of corn starch and 0.3 parts of magnesium stearate were mixed. The mixture was compressed into tablets weighing 70 mg per tablet. Each tablet had a diameter of 5.5 mm and contained 30 mg of pyridoxal phosphate. The hardness of the tablet as determined with a Heberlein hardness tester was 4.7 kg and the disintegration time according to the method of Japanese Pharmacopeia was 3.5 minutes.

EXAMPLE 12

22.2 parts of pyridoxine hydrochloride-containing granules as obtained in Example 2, 22.2 parts of calcium pantothenate-containing granules as obtained in Example 6, 2.2 parts of thiamine nitrate-containing granules (prepared according to Example 2 of European Patent (Laid-Open) No. 0178138), 22.2 parts of nicotinamide-containing granules as obtained in Example 4, 0.3 parts of 0.1% cyanocobalamin trituration, 10.4 parts of crystalline cellulose and 0.5 parts of magnesium stearate were mixed. The mixture was compressed into tablets weighing 700 mg per tablet. Each tablet had a diameter of 13.0 mm and contained 150 mg of thiamine nitrate, 150 mg of pyridoxine hydrochloride, 150 mg of nicotinamide, 150 mg of calcium pantothenate, and 150 mcg of cyanocobalamin. The tablet had a hardness of 15 kg as measured with a Heberlein hardness tester and showed a disintegration time of 21 minutes as tested by the method according to the Japanese Pharmacopeia.

EXAMPLE 13

5.4 parts of pyridoxine hydrochloride-containing granules as obtained in Example 1, 5.4 parts of thiamine nitrate-containing granules (prepared based on Example 2 of European Patent (Laid-Open) No. 0178138, thiamine nitrate content 97 weight %, hydroxypropylmethylcellulose content 3 weight %), 5.4 parts of nicotinamide-containing granules as obtained in Example 5, 5.4 parts of riboflavin-containing granules as obtained in Example 7, 51.0 parts of ascorbic acid-containing granules (prepared based on Example 3 of U.S. Pat. No. 4,036,948, ascorbic acid content 97 weight %, hydroxypropylmethylcellulose content 3 weight %) 6.7 parts of calcium pantothenate-containing granules as obtained in Example 6, 1.5 parts of 0.1% cyanocobalamin trituration 12.4 parts of crystalline cellulose, 20.3 parts lactose and 0.5 parts of magnesium stearate were mixed.

The mixture was compressed into capsular tablets weighing 1140 mg per tablet. Each tablet had a length of 19 mm in major axis and 8 mm in minor axis, and contained 50 mg of thiamine mononitrate, 50 mg of riboflavin, 50 mg of pyridoxine hydrochloride, 50 mg of nicotinamide, 10 mcg of cyanocobalamin, 50 mg of calcium pantothenate and 500 mg of ascorbic acid. The tablet had a hardness of 15.6 kg as measured with a Heberlein hardness tester and showed a disintegration time of 21 minutes as tested by the method according to the Japanese Pharmacopeia.

EXAMPLE 14

0.55 parts of riboflavin-containing granules as obtained in Example 7, 56.5 parts of calcium ascorbate-containing granules as obtained in the Reference Example, 51 parts of ascorbic acid-containing granules (prepared based on Example 3 of U.S. Pat. No.4,036,948, ascorbic acid content 97 weight %, hydroxypropylmethylcellulose content 3 weight %), 11.9 parts of crystalline cellulose, and 0.6 parts of magnesium stearate were mixed. The mixture was compressed into tablets having a weight of 121 mg per tablet. The tablet had a diameter of 6.5 mm and contained 100 mg of vitamin C and 5 mg of riboflavin. The hardness of the tablet as determined with a Heberlein hardness tester was 6.5 kg and the disintegration time was 18 minutes according to the method of Japanese Pharmacopeia.

We claim:

1. A vitamin-containing granule comprising one or more compounds selected from the group consisting of vitamin $B_6$, vitamin $B_2$, nicotinamide and a pantothenic acid salt, and a water-soluble cellulose as a binding agent, said one or more compounds accounting for about 95 to 99 weight percent of the granules on a dry basis.

2. A vitamin-containing granule as claimed in claim 1, wherein the water-soluble cellulose is hydroxypropylcellulose, hydroxymethylcellulose, hydroxypropylmethylcellulose, carboxymethylcellulose or methylcellulose.

3. A vitamin-containing granule comprising one or more compounds selected form the group consisting of vitamin $B_6$, nicotinamide and a pantothenic acid salt, and a water-soluble cellulose as a binding agent, said one or more compounds accounting for about 95 to 99 weight percent of the granules on a dry basis.

4. A vitamin-containing granule comprising vitamin $B_2$, and a water-soluble cellulose as a binding agent, said vitamin $B_2$ accounting for about 95 to 99 weight percent of the granules on a dry basis.

5. A vitamin-containing granule as claimed in claim 1, wherein the water-soluble cellulose is hydroxymethylcellulose.

6. A vitamin-containing granule as claimed in claim 1, wherein the water-soluble cellulose is hydroxypropylcellulose.

7. A vitamin-containing granule as claimed in claim 1, wherein the water-soluble cellulose is hydroxypropylmethylcellulose.

8. A tablet containing granules comprising one or more compounds selected from the group consisting of vitamin $B_6$, vitamin $B_2$, nicotinamide, and a slat of pantothenic acid, and a water-soluble cellulose as a binding agent, said one or more compounds accounting for about 95 to 99 weight percent of the granules on a dry basis.

* * * * *